United States Patent [19]
Hoffman

[11] 4,179,815
[45] Dec. 25, 1979

[54] DENTAL DEVICE
[75] Inventor: Carl S. Hoffman, Cheshire, Conn.
[73] Assignee: TP Laboratories, Inc., LaPorte, Ind.
[21] Appl. No.: 865,526
[22] Filed: Dec. 29, 1977
[51] Int. Cl.$^2$ ............................................... A61C 5/14
[52] U.S. Cl. ........................................ 433/140; 128/12
[58] Field of Search ............................ 128/12, 15, 20; 32/40 R, 35

[56] References Cited
U.S. PATENT DOCUMENTS

| 735,762 | 8/1903 | Hare | 128/15 |
| 2,220,674 | 11/1940 | Bloomheurt | 128/12 |
| 2,797,682 | 7/1957 | Kannenberg | 128/2 |

Primary Examiner—Robert Peshock
Attorney, Agent, or Firm—Lloyd L. Zickert

[57] ABSTRACT

A dental device including a body of plastic material having a plurality of bite block portions and a tongue shield portion for holding a patient's mouth open while restricting movement of the tongue toward the teeth. The bite block portions are adapted to be engaged by the opposing occlusal surfaces of the arches and the tongue shield portion extends between the bite block portions for particularly blocking the tongue from moving toward the lingual surfaces of the teeth.

5 Claims, 7 Drawing Figures

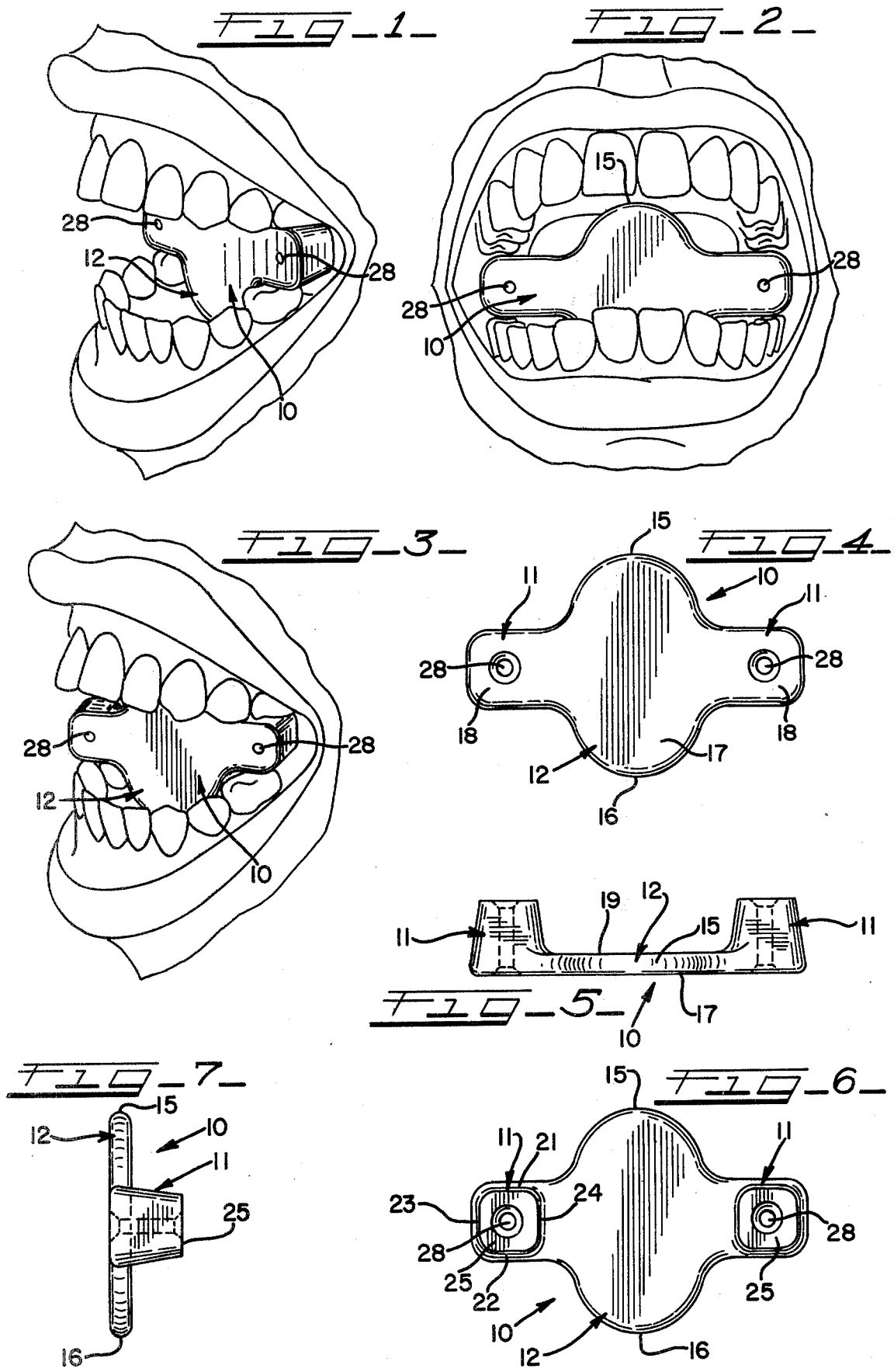

DENTAL DEVICE

This invention relates in general to a dental device, and more particularly to a dental device for facilitating dental and medical procedures utilized in treating the mouth of a patient, and still more particularly to a dental device for holding open the mouth of a patient by maintaining in spaced relation the upper and lower dental arches and preventing movement of the tongue toward the lingual surfaces of the teeth.

Heretofore, it has been well known to provide bite blocks or mouth props for maintaining the mouth of a patient open wherein the bite blocks would be positioned between and engaged by the upper and lower dental arches of a person to thereby facilitate dental or medical procedures employed during treatment of the mouth. These bite blocks have been designed for engagement by the arches at one side of the mouth. Use of such a prop does not prevent moisture contamination of the teeth by the tongue. It has also been known to provide cheek extractors or expanders for facilitating the employment of dental and medical procedures in connection with the mouth, and it has been known to provide a cheek expander and tongue retractor appliance which restricts movement of the tongue while maintaining the cheeks in expanded position, as shown in U.S. Pat. No. 4,002,162. This appliance does not prop open the arches making it necessary for the patient to use the jaw muscles to hold the arches open, which after a period of time causes considerable discomfort.

The present invention is an improvement over the prior art in that it provides the dual purpose of propping the mouth open and preventing the tongue from touching or engaging the lingual surfaces of the teeth to facilitate the employment of dental or medical procedures on the mouth, while at the same time preventing moisture contamination of the teeth by the tongue and promoting patient comfort. It will be appreciated the work of the medical or dental professional is made much easier and is accomplished more efficiently when the desired mouth conditions are achieved and the patient is the most comfortable. It is particularly important to maintain a moisture-free condition of teeth being treated for cavities or having orthodontic appliances directly bonded thereto.

It is difficult and sometimes impossible for many patients to hold their mouths open during medical or dental treatment when it is necessary to do so for a long period of time. Many of the medical or dental procedures employed for treating the mouth of a patient require considerable time to complete. Accordingly, holding the mouth open for such a time can cause much patient discomfort. An uncomfortable patient impairs medical or dental treatment. However, it is also important to conduct medical and dental procedures in the mouth under the best possible conditions. In this respect the tongue often impedes the work of the professional. Particularly, as above noted, direct bonding of orthodontic appliances to the teeth and cavity filling of teeth require freedom from moisture conditions and particularly moisture contamination from the tongue.

The present invention solves the problems of patient discomfort and moisture contamination from the tongue by preventing the tongue from moving toward the teeth while at the same time propping the mouth open allowing the patient to relax the jaw muscles. The anterior teeth are then maintained free from tongue engagement and particularly the lingual surfaces of the teeth are maintained free from contamination. In this respect the dental device of the present invention is a combination mouth prop tongue holder for effecting the dual purpose of comfortably propping the mouth in an open position and preventing the tongue from touching the lingual surfaces of the teeth.

The dental device of the present invention is molded of non-toxic FDA approved plastic material with generally smooth and rounded surfaces to enhance patient comfort. The device includes a body having a pair of spaced-apart bite block portions interconnected by a tongue shield portion. The bite block portions are generally rectangular in cross section and particularly generally square in cross section and may be formed with a slight taper so as to facilitate fitting between the arches. The tongue shield portion extending between the bite block portions is somewhat oval in shape so that it can extend within the areas of the dental arches at the lingual sides of the teeth and completely block forward movement of the tongue. A hole is provided through each of the bite blocks for purposes of facilitating grasping by a bird-peak pliers or the like to enable ease of placement within or removal from the mouth. Further, the hole can be used for the purpose of tying a safety string to the device to guard against any possible inhaling of swallowing of the device by a patient.

It is therefore an object of the present invention to provide a new and improved dental device for facilitating the treatment of a person's mouth by propping the mouth open and restricting tongue movement.

Another object of this invention is in the provision of a new and improved dental device molded of an FDA approved translucent plastic material which includes a plurality of bite blocks interconnected by a shield for accomplishing the dual purpose of propping the mouth open and preventing the tongue from touching the teeth and particularly the anterior teeth to allow medical and dental treatment of the mouth.

A still further object of this invention is in the provision of providing an improved dental device which is particularly used for direct bonding of orthodontic appliances to teeth and which prevents moisture contamination from the tongue and patient discomfort.

Other objects, features and advantages of the invention will be apparent from the following detailed disclosure, taken in conjunction with the accompanying sheet of drawings, wherein like reference numerals refer to like parts, in which:

FIG. 1 is a perspective view of the mouth of a person in open position and having the dental device of the present invention in the mouth for holding the mouth open and preventing the tongue from engaging the lingual surfaces of the teeth, and looking at the mouth from generally a side view;

FIG. 2 is a front elevational view of the mouth of a person in open position and with the dental device of the present invention in place;

FIG. 3 is a view like FIG. 1 but showing the dental device in angulated position relative the mouth for better exposing of the rear teeth on one side;

FIG. 4 is a front elevational view of the dental device of the present invention;

FIG. 5 is a top plan view of the dental device;

FIG. 6 is a rear elevational view of the dental device; and

FIG. 7 is an end elevational view of the dental device.

Referring now to the drawings, and particularly to FIGS. 1, 2 and 3, the dental device of the present invention, generally indicated by the numeral 10, is shown in position within the mouth of a person functioning to hold open or prop open the mouth and the arches and to block or prevent the tongue from engaging the lingual surfaces of the teeth anterior of the device. The dental device of the invention is shown in detail outside of the mouth in FIGS. 4 to 7.

The device includes a one-piece body of molded plastic material having a pair of bite block portions or mouth prop portions 11 arranged in spaced-apart relation and interconnected by a shield portion 12. For convenience hereafter the bite block portions 11 may be referred to as bite blocks or mouth props, while the shield portion may be referred to as a shield. The device is molded from a non-toxic FDA approved translucent plastic material such as a thermoplastic which allows the device to be re-usable and cold sterilized.

The bite blocks 11 are generally rectanguar in cross-sectional shape and particularly square in cross-sectional shape although it should be appreciated that they may take any other desired cross-sectional configuration. It has been found that the shape illustrated provides the best possible control of the device in the mouth during engagement by the arches. Further, the bite blocks 11 are tapered slightly from the shield 12 rearwardly or posteriorly so that a better fit will be accomplished when the arches engage the surfaces of the bite blocks. The longitudinal axes of the bite blocks are perpendicular to the plane of the shield portion as particularly shown in FIG. 7, although it can be appreciated that the bite block axes need only be generally perpendicular to the tongue shield portion.

The sizing of the bite blocks may vary as well as the sizing of the tongue shield. However, the relative proportions as illustrated are satisfactory for most applications. Increasing the size of the bite blocks would assist in propping the mouth in a further ope position and would permit the device to be placed more anteriorly between the arches. However, it can be appreciated that spacing of the arches is regulated by the position of the device within the mouth. For example, if the device is positioned in the forwardmost part of the mouth, the mouth would not be propped open as far as if it were positioned further back or in the farthest posterior portion of the mouth.

The tongue shield 11 is generally oval in shape, while the bite blocks are integral with the opposite long sides of the shield. Accordingly, the shield 11 includes upper and lower arcuately formed ends 15 and 16, as seen in FIG. 4, which define arcuately formed edges in cross section, as shown in FIG. 7. As illustrated in FIGS. 1, 2 and 3, the upper and lower end portions of the tongue shield extend within the upper and lower arches at the lingual side of the teeth, so as to properly perform blocking movement of the tongue, thereby eliminating moisture contamination at the lingual surfaces of the teeth and possible interference of the tongue with any medical or dental procedures used in treatment. The anterior or forward surface 17 of the tongue shield is flush with the anterior or forward surfaces 18 of the bite blocks 11. It can further be seen in FIG. 5 that the bite blocks 11 extend posteriorly or rearwardly of the rearward or posterior face 19 of the tongue shield. While the tongue shield 12 is illustrated as being flat, it may be appreciated that it may be otherwise formed such as being slightly curvate along the vertical and/or horizontal.

The bite blocks 11 or mouth props effectively extend rearward from the tongue shield 12, as shown particularly in FIGS. 5 and 7. Further, the bite blocks are illustrated as being rectangular in shape and generally square in cross section, as seen particularly in FIG. 6, although it should be appreciated that they may take any desired cross-sectional configuration. Each bite block 11 as illustrated includes upper and lower planar surfaces 21 and 22 which extend generally horizontally as viewed in FIG. 6 and in converging relation with each other from the shield to their distal or rearward ends. Each bite block also includes opposed buccal and lingual surfaces 23 and 24 which likewise converge toward one another from the shield portion to their distal ends of the bite blocks. Accordingly, the surfaces 21, 22, 23 and 24 define the bite blocks as having a slight taper toward their posterior or rearward faces 25. The upper and lower surfaces 21 and 22 of each bite block will be engaged by the occlusal surfaces of each of the upper and lower dental arches, as illustrated in FIGS. 1 to 3.

A further feature is the provision of holes 28 extending through the bite blocks and along the longitudinal axes which serve to permit the grasping of either bite block by a jaw of a plier, such as a bird-beak plier, for placement of the device within the mouth of a patient or removal therefrom. However, it can be appreciated that the fingers of the professional could be used for placement and removal of the device within the mouth of a patient. Further, the hole may be used so that a safety string may be tied to one of the bite blocks, which would be a safeguard against the swallowing or inhalation of the device by a patient.

It now can be appreciated from the foregoing that the dental device of the invention can be used for propping open the mouth of a patient and preventing movement of the tongue toward the lingual surfaces of the teeth. The extent of the opening between the upper and lower arches would depend upon the depth of placement of the device. When in place, the teeth would engage the bite blocks and would allow the jaw muscles of the patient to comfortably relax while still holding the arch in an open position as illustrated in FIGS. 1 to 3. Elimination of patient discomfort renders the job of the medical practitioner more efficient and easy to accomplish. For example, a dentist wanting to directly bond an orthodontic appliance to the labial or buccal surfaces of the anterior teeth would be able to maintain the lingual surfaces of the teeth free from moisture contamination by using the dental device of the invention. The work of the dentist would thereby be made much easier, and the comfort of the patient would be materially enhanced relative to a situation where it would be necessary for the patient to constantly tension his muscles to maintain the mouth in an open position. It can also be appreciated that the device may be positioned squarely in the mouth, as shown in FIGS. 1 and 2, or at an angle, as shown in FIG. 3, so as to expose more posterior teeth along one side of the mouth.

It will be understood that modifications and variations may be effected without departing from the scope of the novel concepts of the present invention, but it is understood that this application is to be limited only by the scope of the appended claims.

The invention is hereby claimed as follows:

1. A dental device molded of thermal plastic material, natural or synthetic rubber, for holding open a patient's mouth and restricting tongue movement, which comprises a plurality of spaced generally box-shaped and rectangular in cross section bite blocks adapted to be engaged by occlusal surfaces of the upper and lower arches, and a shield extending between said bite blocks adapted to restrict movement of the tongue, said shield extending above and below the bite blocks and generally vertically when the device is placed within the mouth to prevent the tongue from engaging the lingual surfaces of the anterior teeth and further including an anterior face flush with the anterior ends of the bite blocks, and the posterior ends of the bite blocks extending posteriorly of the posterior face of the shield.

2. A dental device as defined in claim 1, wherein said plastic material is non-toxic and FDA approved.

3. A dental device as defined in claim 1, wherein each bite block includes a hole therethrough to facilitate gripping with a bird-beak plier for placement and removal of the device or for tying a safety string thereto.

4. A dental device for propping open a patient's mouth and preventing the tongue from touching the lingual surfaces of the anterior teeth of the patient to facilitate direct bonding of appliances onto the anterior teeth, said device comprising a one-piece body of molded FDA approved plastic, said body including a pair of spaced bite block portions for engagement by the occlusal surface of the upper and lower arches, and a shield portion extending between said bite block portions for preventing the tongue from engaging the lingual surfaces of the anterior teeth and extending generally vertically when the device is placed within the mouth of the patient, said bite block portions extending posteriorly from the said shield portion and being generally square in cross section and tapered from the shield portion posteriorly.

5. A dental device as defined in claim 4, wherein each bite block portion includes a hole therethrough to facilitate gripping with a bird-beak plier for placement and removal of the device or for tying a safety string thereto.

* * * * *